(12) United States Patent
Nayak et al.

(10) Patent No.: US 10,774,418 B2
(45) Date of Patent: Sep. 15, 2020

(54) SYSTEMS AND METHODS TO IMPROVE OPTICAL SPECTRUM FIDELITY IN INTEGRATED COMPUTATIONAL ELEMENTS

(71) Applicant: Halliburton Energy Services, Inc., Houston, TX (US)

(72) Inventors: Aditya B. Nayak, Houston, TX (US); James M. Price, Spring, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/440,504

(22) PCT Filed: Dec. 23, 2013

(86) PCT No.: PCT/US2013/077569
§ 371 (c)(1),
(2) Date: May 4, 2015

(87) PCT Pub. No.: WO2015/099671
PCT Pub. Date: Jul. 2, 2015

(65) Prior Publication Data
US 2016/0289821 A1    Oct. 6, 2016

(51) Int. Cl.
*C23C 14/54*  (2006.01)
*G01B 11/06*  (2006.01)
(Continued)

(52) U.S. Cl.
CPC ............ *C23C 14/547* (2013.01); *C23C 14/14* (2013.01); *C23C 14/30* (2013.01); *E21B 49/08* (2013.01);
(Continued)

(58) Field of Classification Search
CPC ... C23C 14/547; C23C 14/541; C23C 14/545; C23C 14/50; G01N 21/31;
(Continued)

(56) References Cited

U.S. PATENT DOCUMENTS 5,144,498 A * 9/1992 Vincent ............... G01J 3/12
250/226
6,503,578 B1 * 1/2003 Yeh ............... C23C 14/0629
427/162

(Continued)

FOREIGN PATENT DOCUMENTS

WO    2010085496    7/2010

OTHER PUBLICATIONS

Extinction Coefficient, https://en.wikipedia.org/wiki/Refractive_index_and_extinction_coefficient_of_thin_film_materials accessed online Feb. 5, 2018.*
(Continued)

*Primary Examiner* — Michael P Wieczorek
*Assistant Examiner* — Michael G Miller
(74) *Attorney, Agent, or Firm* — Chamberlain Hrdlicka (57) ABSTRACT

Systems and methods are disclosed for improving optical spectrum fidelity of an integrated computational element fabricated on a substrate. The integrated computational element is configured, upon completion, to process an optical spectrum representing a chemical constituent of a production fluid from a wellbore. The systems and methods measure in situ a thickness, a complex index of refraction, or both of a film formed during fabrication to generate a predicted optical spectrum. The predicted optical spectrum is compared to a target optical spectrum. Revisions to a design of the integrated computational element are con-
(Continued)

ducted in situ to improve optical spectrum fidelity relative to the target optical spectrum. Other systems and methods are presented.

11 Claims, 6 Drawing Sheets

(51) Int. Cl.

| | | |
|---|---|---|
| *G02B 5/28* | (2006.01) | |
| *G01N 21/41* | (2006.01) | |
| *C23C 14/14* | (2006.01) | |
| *C23C 14/30* | (2006.01) | |
| *E21B 49/08* | (2006.01) | |
| *G01N 21/25* | (2006.01) | |
| *G01N 21/84* | (2006.01) | |
| *G01N 33/28* | (2006.01) | |
| *G02B 1/10* | (2015.01) | |

(52) U.S. Cl.
CPC ...... *G01B 11/0625* (2013.01); *G01B 11/0683* (2013.01); *G01N 21/25* (2013.01); *G01N 21/41* (2013.01); *G01N 21/8422* (2013.01); *G01N 33/28* (2013.01); *G02B 1/10* (2013.01); *G02B 5/281* (2013.01); *G02B 5/285* (2013.01); *G01N 2021/4126* (2013.01)

(58) Field of Classification Search
CPC ............... G01N 33/2823; G01N 21/33; G01N 21/8422; G01N 21/84; G01N 2021/8411; G01N 2021/8438; E21B 49/08
USPC .................................................. 427/160–169
See application file for complete search history.

(56) References Cited

U.S. PATENT DOCUMENTS

| | | | |
|---|---|---|---|
| 7,138,156 B1* | 11/2006 | Myrick | G02B 5/285 |
| | | | 427/10 |
| 8,575,541 B1 | 11/2013 | Jamison et al. | |
| 2002/0093732 A1* | 7/2002 | Knapp | G01J 1/429 |
| | | | 359/361 |
| 2003/0016346 A1 | 1/2003 | Umeda et al. | |
| 2003/0072009 A1* | 4/2003 | Domash | G02B 6/29311 |
| | | | 356/519 |
| 2004/0240093 A1* | 12/2004 | Yoshikawa | C23C 14/0635 |
| | | | 359/883 |
| 2009/0087578 A1* | 4/2009 | Hautala | C23C 14/0605 |
| | | | 427/526 |
| 2009/0213381 A1 | 8/2009 | Appel et al. | |
| 2013/0284900 A1 | 10/2013 | Freese et al. | |
| 2013/0287061 A1 | 10/2013 | Freese et al. | |
| 2013/0323484 A1 | 12/2013 | Pelletier et al. | |

OTHER PUBLICATIONS

NSM Archive, http://www.ioffe.ru/SVA/NSM/Semicond/SiC/optic. html accessed online Feb. 5, 2018.*
Demichelis ("New approach to optical analysis of absorbing thin solid films", F. Demichelis et al, Applied Optics vol. 26 No. 9, May 1, 1987, pp. 1737-1740) (Year: 1987).*
International Search Report and Written Opinion issued in corresponding application PCT/US2013/077569, dated Sep. 22, 2014, 9 pgs.

* cited by examiner

SYSTEMS AND METHODS TO IMPROVE OPTICAL SPECTRUM FIDELITY IN INTEGRATED COMPUTATIONAL ELEMENTS

TECHNICAL FIELD

The present disclosure relates generally to the manufacture of integrated computational elements, and more particularly, to systems and methods to improve optical spectrum fidelity in integrated computational elements fabricated on substrates. The integrated computational elements are configured to enable the measurement of various chemical or physical characteristics of a sample fluid, such as production fluid from a wellbore.

BACKGROUND

In producing fluids from an oil and gas well, it is often advantageous to learn as much about the fluids in the well as possible. In recent times, more and more information is being developed by downhole instruments and tools. Still, additional information and improvements are desired. Quick analysis of other fluids is desirable in other situations.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

In the drawings and description that follow, like parts are typically marked throughout the specification and drawings with the same reference numeral or coordinated numerals. The drawing figures are not necessarily to scale. Certain features of the invention may be shown exaggerated in scale or in somewhat schematic form and some details of conventional elements may not be shown in the interest of clarity and conciseness.

Information about a substance can be derived through the interaction of electromagnetic radiation, e.g., light, with that substance. The interaction changes characteristics of the electromagnetic radiation to form a sample electromagnetic radiation, or interacted electromagnetic radiation; for example, a light may change with respect to frequency (and corresponding wavelength), intensity, polarization, or direction (e.g., through scattering, absorption, reflection or refraction). This sample electromagnetic radiation may be processed to determine chemical or physical characteristics, e.g., chemical, thermal, physical, mechanical, optical or various other characteristics, of the substance. The characteristics can be determined based on the changes in the characteristics of the electromagnetic radiation interacting with the substance. As such, in certain applications, one or more characteristics of crude petroleum, gas, water, or other wellbore fluids can be derived in-situ, e.g., downhole at well sites, as a result of the interaction between these substances and electromagnetic radiation.

Integrated computational elements enable the measurement of various chemical or physical characteristics through the use of regression techniques. An integrated computational element may be formed with a substrate, e.g., an optically-transparent substrate, having multiple stacked dielectric layers, or films (e.g., 2 to 50 or more layers), each having a different refractive index from its adjacent layers. While layers are referenced herein, it should be understood that the integrated computational element is not an optical filter, but an optical processor. Interacted electromagnetic radiation may be optically processed by the integrated computational element in order to isolate a spectrum specific to a chemical constituent. The integrated computational element is operational via reflection, refraction, interference, or a combination thereof to weight the interacted electromagnetic radiation on a per-wavelength basis. The weighting process produces an optical spectrum representative of the chemical constituent.

A spectral weighting is dependent on the thicknesses, complex indices of refraction, and number of layers, or films, in the integrated computational element. Deviations in thickness, complex index of refraction, and number from those specified in a design of the integrated computational element degrade the produced optical spectrum relative to a target optical spectrum. Such degradations in optical spectrum fidelity may negatively impact the accuracy of information obtained about the chemical constituent.

The embodiments described herein relate to systems and methods for improving optical spectrum fidelity of a integrated computational element fabricated on a substrate. Systems and methods are disclosed that, during fabrication, measure in situ a thickness, a complex index of refraction, or both of a film formed during fabrication to generate a predicted optical spectrum. The predicted optical spectrum is produced from an optical model that includes measured characteristics from all formed films and expected characteristics for all unformed films. The predicted optical spectrum is compared to a target optical spectrum. Revisions to a design of the integrated computational element are conducted in situ to improve optical spectrum fidelity relative to the target optical spectrum. Revisions to the design may include revising a thickness, modifying a complex index of refraction, or both of one or more unformed films of the integrated computational element. Other revisions are possible.

As used herein, the term "complex index of refraction" refers to ñ from the relation ñ=n+ik where the real constant, n, is a refractive index of a material and the complex constant, k, is an extinction coefficient of the same material. The refractive index is a dimensionless value that represents the speed of electromagnetic radiation in a material relative to that of a vacuum (i.e., the speed of light, c). The extinction coefficient is a dimensionless value that represents an amount of electromagnetic radiation absorbed while propagating through the material. While not intending to be limited by theory, the real and imaginary parts of the complex refractive index are related via Kramers-Kronig relationship; a change in extinction coefficient implies a change in the real part of the complex refractive index too.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to". Unless otherwise indicated, as used throughout this document, "or" does not require mutual exclusivity. As used herein, "in situ" means in the manufacturing vessel.

Figure 1:
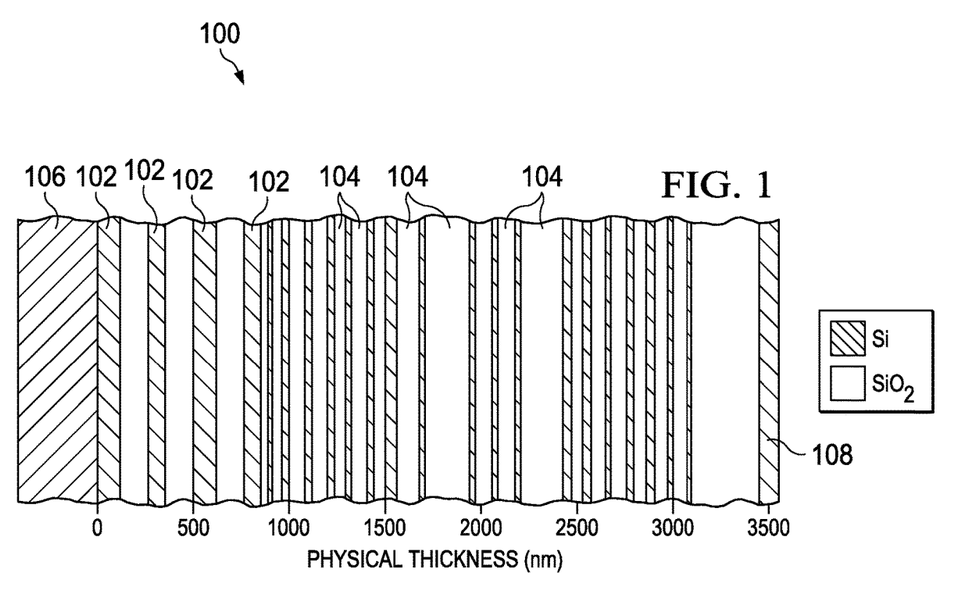
FIG. 1 is a cross-sectional view of a portion of an illustrative embodiment of an integrated computational element for processing an optical spectrum representing a chemical constituent of a production fluid from a wellbore.

Now referring primarily to FIG. 1, a cross-sectional view of a portion of an illustrative embodiment of an integrated computational element 100 for processing an optical spectrum is shown. The integrated computational element 100 may include alternating layers of high refractive index 102 and low refractive index 104 materials. In the embodiment illustrated by FIG. 1, the layers of high refractive index 102 are formed of silicon and those of low refractive index 104, silicon dioxide. This embodiment, however, is not intended as limiting. The layers 102 may be formed of other materials that have a high refractive index. Non-limiting examples of such materials include germanium, aluminum arsenide, gallium arsenide, indium phosphide, silicon carbide, dielectrics (e.g., titanium dioxide), and other semiconductor materials. Similarly, the layers 104 may be formed of other materials that have a low refractive index. Non-limiting examples of these materials include germanium dioxide, magnesium fluoride, and aluminum oxide. The number of layers, and the materials used for each layer, of different refractive indices in integrated computational element 100 are representative and should not be considered limiting. For example, without limitation, the integrated computational element 100 may be comprised of three or more materials with different refractive index The integrated computational element 100 is fabricated on a substrate 106, e.g., an optically-transparent substrate, to provide support for the layers 102, 104. The substrate 106 may be a single crystal, a polycrystalline ceramic, an amorphous glass, or a plastic material. In some embodiments, the substrate 106 is formed of BK-7 optical glass. In other embodiments, the substrate 106 may be quartz, diamond, sapphire, silicon, germanium, magnesium fluoride, aluminum nitride, gallium nitride, zinc selenide, zinc sulfide, fused silica, polycarbonate, polymethylmethacrylate (PMMA), or polyvinylchloride (PVC). Other substrates are possible. In still other embodiments, the integrated computational element 100 includes an optional capping layer 108 that, during operation, is exposed to the production fluid.

The layers 102 and 104, the substrate 106, and the capping layer 108 (if present) function in combination as an integrated computational element. The integrated computational element optically processes an electromagnetic radiation according to a spectral weighting (i.e., a wavelength-dependent weighting). In operation, the interacted electromagnetic radiation from the sample enters and interacts with the integrated computational element 100. The layers 102, 104 induce reflection, refraction, interference, or a combination thereof within the integrated computational element 100 to alter an intensity of the electromagnetic radiation on a per-wavelength basis. The electromagnetic radiation exits the integrated computational element as a weighted optical spectrum whose individual wavelengths have been proportionately processed by the integrated computational element 100.

The spectral weighting is controlled by a thickness, a complex index of refraction, and a number of individual layers 102, 104 of the integrated computational element 100. The thickness, the refractive index (i.e., material), and the number of layers may be selected according to a design of the integrated computational element 100 to characterize a chemical constituent or property of the production fluid or other fluid to be analyzed. For example, the integrated computational element 100 may be used downhole to allow production fluids downhole to be quickly analyzed.

During analysis of the production fluid, electromagnetic radiation is passed through the production fluid and delivered to an integrated computational element incorporating the design to produce sample interacted electromagnetic radiation, or sample interacted radiation. Interaction of the electromagnetic radiation with the production fluid allows the electromagnetic radiation to acquire optical characteristics that represent attributes of the production fluid. Subsequent optical processing of the sample interacted radiation by the integrated computational element allows determination of a desired information about the chemical constituent (e.g., concentration) in the fluid. The resultant information is transmitted to the surface, stored locally, or both.

It should be understood that the design shown in FIG. 1 does not necessarily correspond to any particular chemical constituent, but is provided for purposes of illustration only. Furthermore, the layers 102, 104 and their relative thicknesses are not necessarily drawn to scale, and therefore should not be considered limiting of the present disclosure. The number of layers 102, 104, their relative thicknesses, and their materials of construction, as shown in FIG. 1, may bear little correlation to any particular characteristic of a production fluid.

Figure 2:
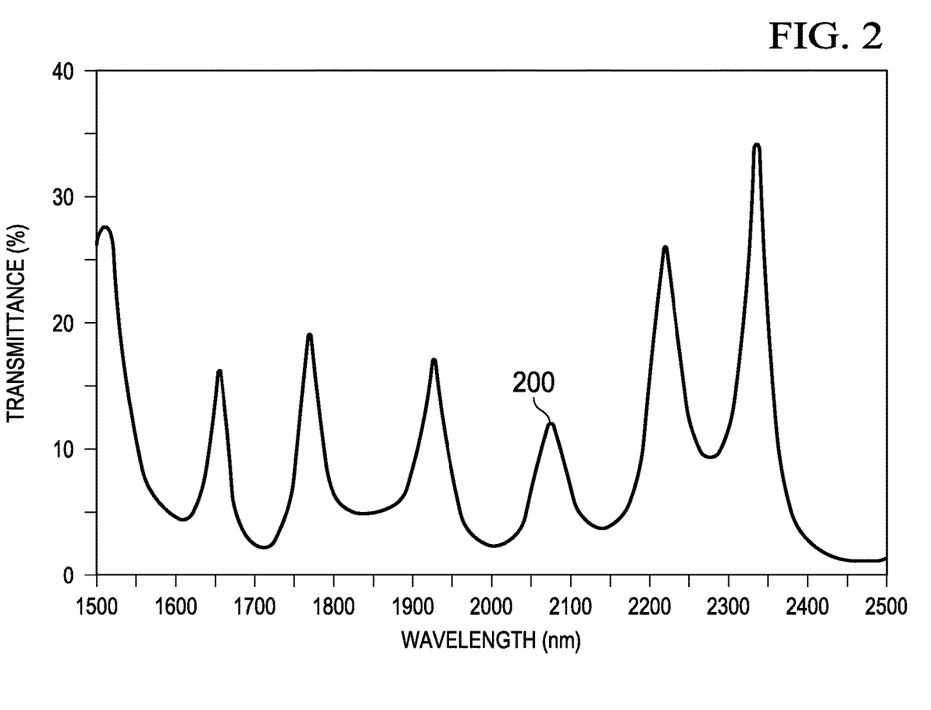
FIG. 2 is graph representing a variation of optical transmittance with wavelength for an integrated computational element according to an illustrative embodiment.
Figure 3:
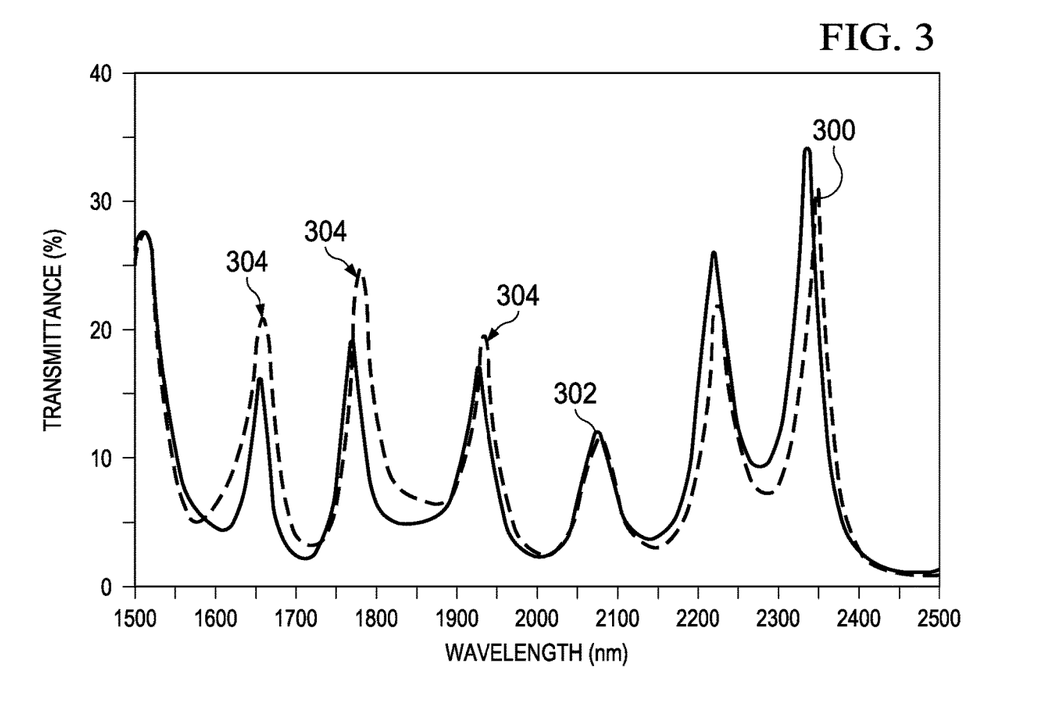
FIG. 3 is a graph representing a variation of optical transmittance with wavelength for the integrated computational element of FIG. 2, but where one film thickness is deviated from that specified in the design.
Figure 4:
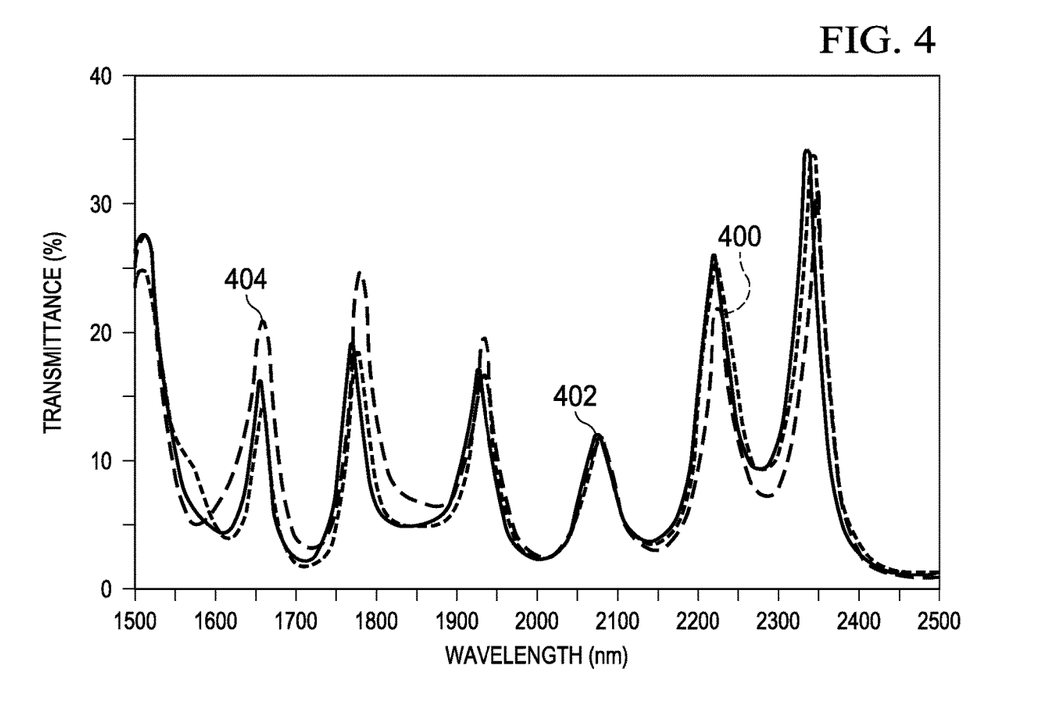
FIG. 4 is a graph representing a variation of optical transmittance with wavelength for the deviated integrated computational element of FIG. 3, but where a complex index of refraction for a subsequent film has been altered.

Deviations in thickness, refractive index, and number of layers from that specified in the design will degrade the spectral weighting desired from the integrated computational element. The accuracy of information related to the chemical constituent (e.g., concentration) obtained from any weighted optical spectrum is thereby reduced. FIGS. 2-4 present an illustrative example where a deviation in thickness alters a spectral weighting of an integrated computational element. The alteration manifests itself as a loss in optical spectrum fidelity relative to a target optical spectrum. With this information, the design of the integrated computational element is subsequently revised to compensate for the deviation in thickness thereby improving optical spectrum fidelity. For example, a complex index of refraction is selected to bring the weighted optical spectrum in closer congruence with the target optical spectrum.

Now referring to FIG. 2, a variation of optical transmittance 200 with wavelength is depicted for an integrated computational element according to one illustrated embodiment. The variation of optical transmittance 200 is generated using an optical model of the integrated computational element. The optical model is developed from a design of the integrated computational element which specifies, in part, the number of individual layers, their thicknesses, and their complex indices of refraction. Other specifications are possible. For the integrated computational element of FIG. 2, the design includes seven alternating films of silicon and silicon dioxide fabricated on an optically-transparent substrate of BK-7 glass. Films of silicon start and terminate the integrated computational element. The variation of optical transmittance 200 represents a target optical spectrum for the integrated computational element fabricated according to the design. In this example, the design has been selected so that the target optical spectrum corresponds to a methane concentration in a production fluid.

Now referring to FIG. 3, a variation of optical transmittance 300 with wavelength is shown for the integrated computational element of FIG. 2 but where one film thickness is deviated from that specified in the design. Specifically, the silicon dioxide film below the top silicon film is increased in thickness by 25%. Such a deviation may result, for example, from a manufacturing fault during fabrication (e.g., over-deposition of a film). The variation of optical transmittance 300 is shown relative to the variation of optical transmittance 302 originally depicted in FIG. 2. The 25% increase in thickness clearly results in a loss of optical spectrum fidelity as evidenced by multiple peak height differences 304 at approximately 1650 nm, 1775 nm, and 1925 nm.

Now referring to FIG. 4, a variation of optical transmittance 400 with wavelength is presented for the deviated integrated computational element of FIG. 3, but where the complex index of refraction for one subsequent film has been subsequently altered. Specifically, the extinction coefficient of the top silicon film has been increased 50% to compensate for the 25% increase in thickness of the underlying silicon dioxide film. The variation of optical transmittance 400 (i.e., a dotted curve) is presented relative to the variation of optical transmittance 402 originally depicted in FIG. 2 (i.e., a solid curve) and the variation of optical transmittance 404 originally shown in FIG. 3 (i.e., a dashed curve). The variation of optical transmittance 400 nearly overlaps the target optical spectrum of the design (i.e., the variation of optical transmittance, 402). Thus, the increase in extinction coefficient has served to improve the optical spectrum fidelity of the integrated computational element relative to the target optical spectrum.

The illustrative example of FIGS. 2-4 is provided in the context of a optical model of an integrated computational element and its associated optical spectrum. However, this context is not intended as limiting. The systems and methods presented herein enable in situ revisions to a design of an integrated computational element during fabrication. Revisions to the design are made to improve optical spectrum fidelity relative to a target optical spectrum. Such revisions include selecting a thickness, a complex index of refraction, or both for one or more unformed films of the integrated computational element. Furthermore, revisions to the design may occur iteratively after each film of the integrated computational element is formed. The unformed layers of the integrated computational element are then deposited using updated specifications from the revised design.

Figure 5:
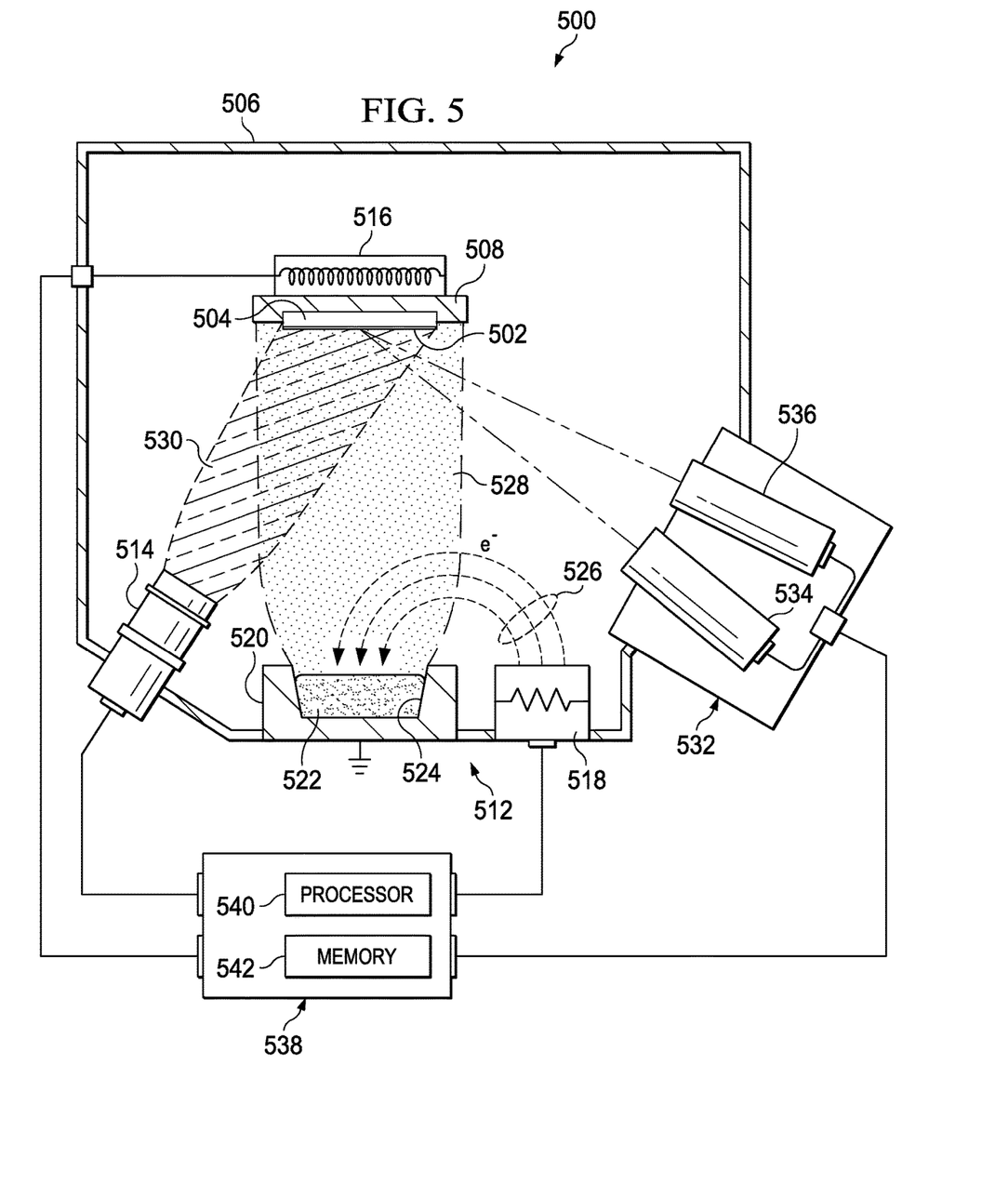
FIG. 5 is a schematic diagram of an illustrative embodiment of a fabrication system for improving optical-spectrum fidelity of a integrated computational element fabricated on an optically transparent substrate.

Now referring primarily to FIG. 5, a schematic diagram of an illustrative embodiment of a fabrication system 500 for improving optical-spectrum fidelity of an integrated computational element 502 fabricated on a substrate 504, e.g., an optically transparent substrate, is presented. The integrated computational element 502 is fabricated to transmit an optical spectrum representing a chemical constituent of a production fluid from a wellbore or other fluid. The fabrication system 500 includes a chamber 506, or vessel, and a substrate holder 508. In some embodiments, the vessel or chamber may be placed a low pressure to facilitate deposition, for example, without limitation, ~$E^7$ Torr. The substrate holder 508 secures the substrate 504 within the chamber 506 relative to a mass-flux generator 512 and an ion-beam generator 514. The substrate holder 508 may include an optional heater 516 for raising and maintaining a temperature of the substrate 504 above ambient. The optional heater 516 in some embodiments may not be coupled to the substrate 504 as such. For example, in one embodiment heating lamps, e.g., halogen lamps, inside the chamber 506 are used to uniformly heat the entire chamber 506 and substrate 504 to a desired temperature. The mass-flux generator 512 is coupled to the chamber 506 and includes an electron gun 518 and a crucible 520 for heating a mass source 522. The mass source 522 is contained within a pocket 524 of the crucible 520 and sits adjacent the electron gun 518.

The electron gun 518 is configured to generate a beam of electrons 526 from a filament and arc the beam of electrons 526 into the pocket 524 of the crucible 520 via a magnetic field. Energy from the beam of electrons 526 is absorbed by the mass source 522 producing heat which induces evaporation of the mass source. A water-cooling circuit (not shown) is typically incorporated into the crucible 520 to prevent the crucible 520 from decomposing or melting. The crucible 520 is electrically grounded. Evaporation of the mass source 522 is operable to generate a mass flux 528 that is received by the substrate holder 508.

The mass flux 528 may include elements, molecules, or a combination thereof. Impingement of the mass flux 528 onto the substrate 504, or onto existing films already formed on the substrate 504, allows the fabrication system 500 to form a film of the integrated computational element 502. In some embodiments, the crucible 520 contains two or more pockets 524 for holding two or more different mass sources 522. In such embodiments, the electron gun 518 arcs the beam of electrons 526 into the appropriate pocket 524 to heat the desired mass source 522. This configuration may allow the fabrication system 500 to fabricate a integrated computational element 502 completely without exposing the chamber 506 to an ambient environment (i.e., to introduce a new mass source 522). In other embodiments, the crucible 520 contains two or more pockets 524 for containing mass sources of elemental silicon and silicon dioxide. In these embodiments, the mass-flux generator 512 is operational to form films of, respectively, silicon and silicon dioxide. It should be understood that other techniques may be used; for example, without limitation, two separate electron guns for Si and $SiO_2$ might be used.

The ion-beam generator 514 is configured, during film formation, to produce and direct an ion beam 530 of elements, molecules, or a combination thereof towards the substrate 504. The ion beam 530 impinges upon the forming film and may promote control over film properties such as morphology, density, stress level, crystallinity, and chemical composition. The ion-beam generator 514 may produce the ion beam 530 from a gas source such as oxygen, nitrogen, argon, or a combination thereof. Other gas sources are possible. In some embodiments, the ion-beam generator 514 produces an ion beam 530 using an argon gas source. In other embodiments, the ion-beam generator 514 produces an ion beam 530 using a mixed gas source. The mixed gas source may be pre-mixed before introduction into the chamber 506 or may be mixed in the chamber 506 proximate the ion-beam generator 514. Non-limiting examples of mixed gas sources include argon gas and silane gas; argon gas and methane gas; and argon gas, methane gas, and tetrafluoromethane gas. The aforementioned mixed gas sources are operable to form films of, respectively, hydrogenated amorphous silicon films, films of silicon carbide, and films of silicon carbide alloy, $Si_{1-x-y-z}C_xH_yZ_z$. The compositional boundaries of the silicon carbide alloy are defined by the relation: $x+y+z<1$ where x is non-zero.

Further coupled to or associated with the chamber 506 is a precision measurement device 532. The precision measurement device 532 is oriented towards the substrate 504 and is configured to measure in situ a thickness, a complex index of refraction, or both of a film formed by the mass-flux generator 512. In some embodiments, the precision measurement device 532 includes an ellipsometer 534 for measuring the thickness, the complex index of refraction, or both. In some embodiments, the precision measurement device 532 includes a spectrometer 536 for measuring an optical spectrum of the integrated computational element 502 during fabrication. In some embodiments, the precision measurement device 532 includes a quartz monitor or a single wavelength monitor for thickness. While not explicitly shown, in some embodiments, the precision measurement device 532 includes a probe and a detector that are on opposing sides of the chamber 506 and at the same angle of incidence. While probes, e.g., spectrometer 536 and an ellipsometer, may be coupled on one side of the chamber 506, it should be understood that corresponding detectors may be coupled on the other side of the chamber.

Coupled electrically or communicatively to the mass-flux generator 512 and ion-beam generator 514 is a computational unit 538. The computational unit 538 includes one or more processors 540 and one or more memories 542 to control film formation during fabrication of the integrated computational element 502. The computational unit 538 may be further coupled to the heater 516, if present, to manipulate the temperature of the substrate 504 during fabrication. The computational unit 538 is also coupled to the precision measurement device 532 to control measurement of the thickness, the complex index of refraction, or both of the film formed by the mass-flux generator 512.

In operation, the chamber 506 is evacuated and the electron beam 526 emanated from the electron gun 518. The electron beam 526 is directed into the pocket 524 of the crucible 520 by the magnetic field. Evaporation of the mass source 522 produces the mass flux 528 which traverses a distance from the crucible 520 to the substrate holder 508. The mass-flux generator 512 directs the mass-flux 528 towards the substrate 504 to form a film of the integrated computational element 502. In coordination with the mass-flux generator 512, the ion-beam generator 514 directs the ion beam 530 towards the substrate 504. Such coordination is managed by the computational unit 538 to control film formation during fabrication of the integrated computational element 502. When the film has achieved its desired thickness, the mass-flux generator 512 and the ion-beam generator 514 are deactivated by the computational unit 538. The heater 516, if present, may be functional during the formation process in order to improve film properties. The computational unit 538 regulates the mass-flux generator 512 and the ion-beam generator 514 to form a series of sequential films. A number, thickness, and refractive index (i.e., material) of sequential films in the series is specified by a design of the integrated computational element 502. The design of the integrated computational element 502, when executed to completion, produces alternating layers of high refractive index 102 and low refractive index 104 as shown in the illustrative example of FIG. 1. The capping layer 108 may also be present.

During fabrication of the integrated computational element 502, the computational unit 538 also controls the precision measurement device 532. The precision measurement device 532 is operational to measure in situ a thickness, a complex index of refraction, or both of a formed film of the integrated computational element 502. In some embodiments, the precision measurement device may also measure an optical spectrum of the integrated computational element 502 during fabrication. The computational unit 538 stores into a database the measured thickness, the measured complex index of refraction, or both for all formed films of the integrated computational element. The computational unit 538 also stores into the database an expected thickness, an expected complex index of refraction, or both for all unformed films of the integrated computational element. The expected thickness and expected complex index of refraction of each unformed film is specified by the design of the integrated computational element. In some embodiments, the database is iteratively updated by the computational unit 538 as each new film of the integrated computational element 502 is formed.

The one or more processors 540 and one or more memories 542 of the computational unit 538 are operable to develop or receive an optical model of the as-fabricated integrated computational element from the database. The optical model incorporates measured characteristics of the formed films and expected characteristics of the unformed films. Non-limiting examples of such characteristics include a thickness and a complex refractive index. Other characteristics are possible. In some embodiments, the optical model is iteratively re-developed by the one or more processors 540 and one or more memories 542 as each new film of the integrated computational element 502 is formed. In other embodiments, the model may be based on theoretical calculations, on data from other fabrication operations, or both. The optical model is used by the computational unit 538 to calculate a predicted optical spectrum for the integrated computational element. The predicted optical spectrum is compared to a target optical spectrum, or desired optical spectrum, of the design.

By comparing the predicted optical spectrum against the target optical spectrum, the design can be revised in situ during fabrication to improve optical spectrum fidelity of the integrated computational element 502 at completion. In some embodiments, the computational unit 538 revises the design of the integrated computational element 502 according to a program stored in the one or more memories 540 and executed by the one or more processors 538. Revisions of the integrated computational element may include modifying (e.g., adjusting or selecting) a thickness, a complex index of refraction, or both. Revisions may also include modifying (e.g., adjusting or selecting) a number of unformed films of the integrated computational element. In other embodiments, revision of the design is completed independently by one or more individuals skilled in the art. After revision of the design, the computational unit 538 then continues fabrication of the integrated computational element 502 using the revised design.

Figure 6:
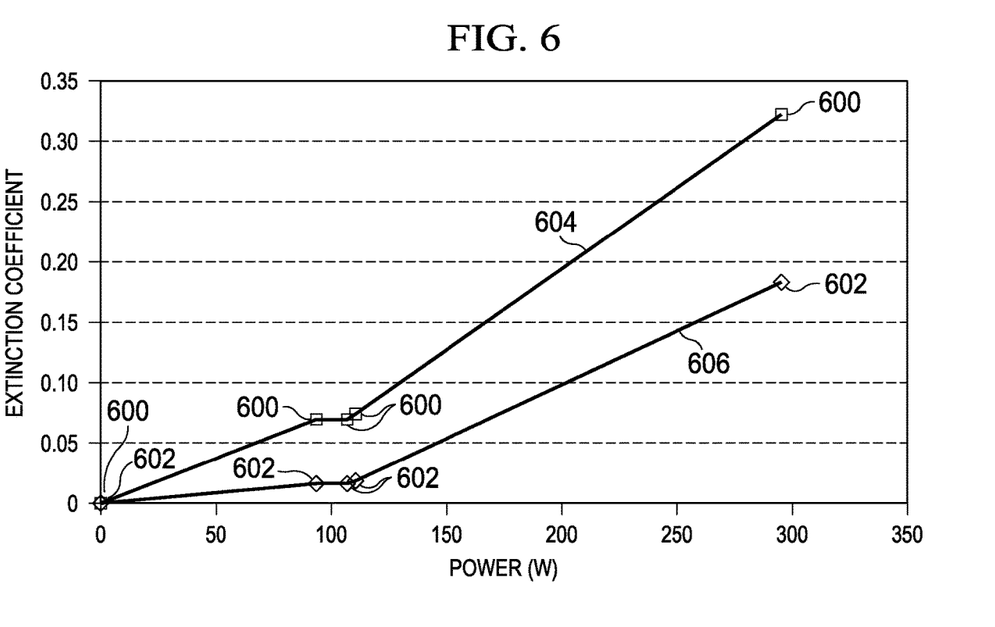
FIG. 6 is a schematic graph of illustrative data representing a dependence of extinction coefficient on power from an ion-beam generator for a silicon film.

It will be appreciated that the fabrication system 500 is capable of revising a design of a integrated computational element in a manner analogous to that presented previously in FIGS. 2-4 and incorporating that revision in situ during fabrication. For example, FIG. 6 shows a variation in extinction coefficient with increasing power from an ion-beam generator according to one illustrative embodiment. The variation in extinction coefficient is measured using silicon films. Individual data points 600, 602 correspond to measurements taken with 950 nm and 1600 nm light, respectively. The respective solid lines 604, 606 indicate an increase in extinction coefficient with power from the ion-beam generator. Thus, the fabrication system 500 may compensate for a deviation in thickness by implementing a raised power of the ion-beam generator 514. The raised power would serve to increase an extinction coefficient of the film according to the revised design. In some embodiments, the power of the ion-beam generator is raised to increase the extinction coefficient of a silicon film during formation, and in others, it could be lowered. It will be appreciated that any of a number of parameters may be modified to influence the performance of the finished integrated computational element.

The fabrication system 500 illustrated in FIG. 5 has been presented in the context of an ion-assisted electron beam deposition system. This illustration, however, is not intended to be limiting. The integrated computational elements presented herein may be fabricated using systems that employ other deposition techniques such as unassisted electron beam evaporation, thermal evaporation, dc-sputtering, dc-magnetron sputtering, rf-sputtering, reactive physical vapor deposition (RPVD), physical vapor deposition (PVD), pulsed laser deposition (PLD), low pressure chemical vapor deposition (LPCVD), plasma-enhanced chemical vapor deposition (PECVD), atmospheric pressure chemical vapor deposition (APCVD), metal organic chemical deposition (MOCVD), and molecular beam epitaxy (MBE). Other deposition techniques are possible.

Figure 7:
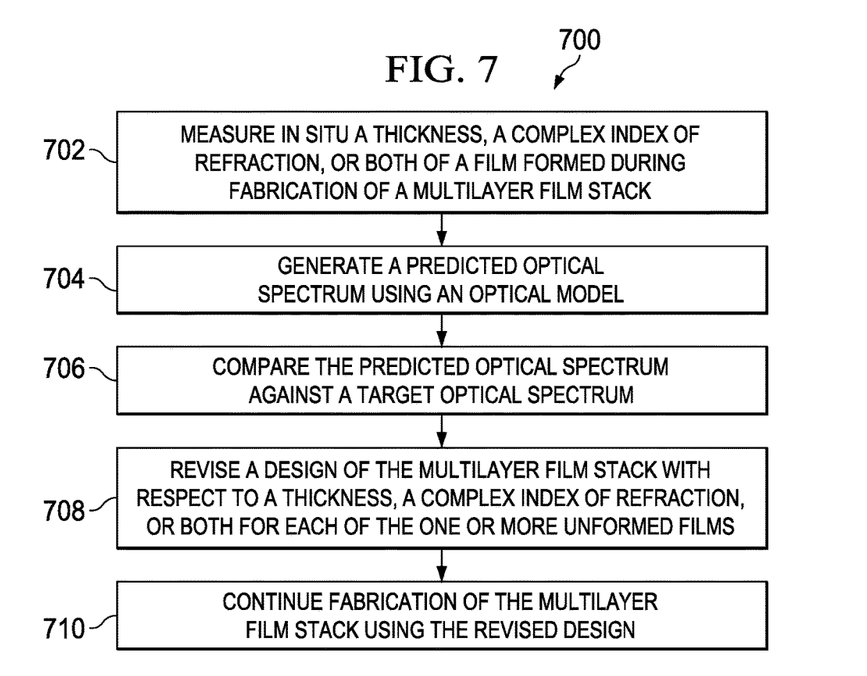
FIG. 7 is a schematic flowchart of an illustrative embodiment of a method for improving optical spectrum fidelity of an integrated computational element fabricated on a substrate.

Now referring primarily to FIG. 7, a schematic flowchart of an illustrative embodiment of a method 700 is presented for improving optical spectrum fidelity of an integrated computational element fabricated on a substrate, e.g., an optically-transparent substrate. The integrated computational element is configured, upon completion, to process an optical spectrum representing a chemical constituent of a production fluid from the wellbore or other fluid. The method 700 includes a step 702 of measuring in situ a thickness, a complex index of refraction, or both of a film formed during fabrication of integrated computational element and a step 704 of generating a predicted optical spectrum using an optical model. The optical model represents the multilayer stack as-fabricated up to the formed film.

The method 700 also includes a step 706 of comparing the predicted optical spectrum against a target optical spectrum. In some embodiments, the predicted optical spectrum includes the formed layers as well as the unformed (i.e., yet to be deposited) layers. In other words, when the system compares the optical spectrum with the target spectrum, it is for the final target spectrum and not the intermediate target spectrum up to the layer deposited. Other embodiments are possible using intermediate information.

The method 700 involves a step 708 of revising a design of the integrated computational element with respect to a thickness, a complex index of refraction, or both for each of the one or more unformed films. The revision is conducted to compensate for any deviation from the target optical spectrum or a desired optical spectrum. The method 700 also involves a step 710 of continuing fabrication of the integrated computational element using the revised design.

In some embodiments, the method 700 further includes iteratively repeating, for each film or additional films formed during fabrication of the integrated computational element, the step 702 of measuring in situ, the step 704 of generating the predicted optical spectrum, the step 706 of comparing the predicted optical spectrum, the step 708 of revising the design, and the step 710 of continuing fabrication. In other embodiments, the step 708 of revising a design and the step 710 of continuing fabrication includes determining a power of an ion-beam generator. In still other embodiments, the step 708 further involves altering the number of unformed films of the integrated computational element.

Figure 8:
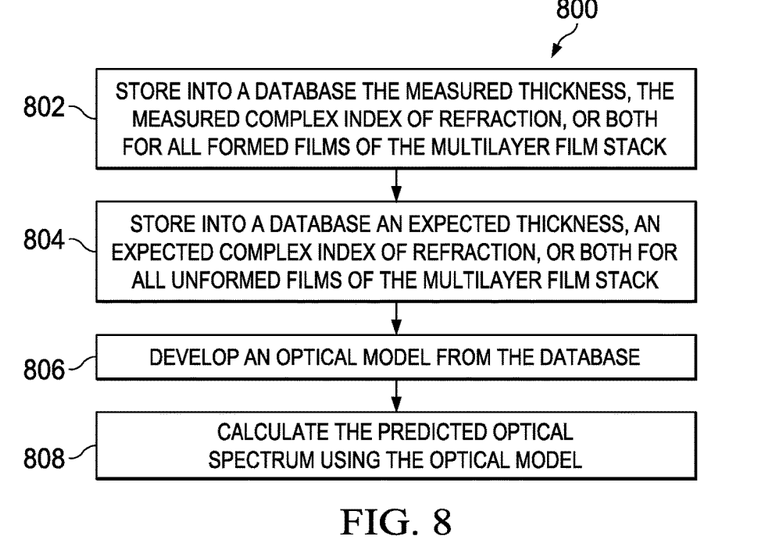
FIG. 8 is a schematic flowchart of an illustrative embodiment of a method for generating a predicted optical spectrum using an illustrative optical model.

Now referring primarily to FIG. 8, but also to FIG. 7, a schematic flowchart of an illustrative embodiment of a method 800 is depicted for generating the predicted optical spectrum using the optical model. The method 800 in FIG. 8 corresponds, according to one embodiment, to the step 704 shown in FIG. 7. The method 800 includes a step 802 of storing into a database the measured thickness, the measured complex index of refraction, or both for all formed films of the integrated computational element and a step 804 of storing into the database an expected thickness, and expected complex index of refraction, or both for all unformed films of the integrated computational element. The expected thickness and expected complex index of refraction of each unformed film is specified by the design of the integrated computational element. The database represents the as-fabricated state of the multilayer films stack. In some embodiments, the database is iteratively updated as each new film of the integrated computational element is formed. The method 800 also includes a step 806 of developing an optical model from the database. The optical model incorporates measured characteristics of the formed films and expected characteristics of the unformed films. Non-limiting examples of such characteristics include a thickness and a complex refractive index. Other characteristics are possible. In some embodiments, the optical model is iteratively re-developed as each new film of the integrated computational element is formed. It will be appreciated that any technique for modeling or predicting performance of the coupled integrated computational element may be used whether theoretical, empirical, or both. The method 800 also involves a step 808 calculating the predicted optical spectrum using the optical model.

Figure 9:
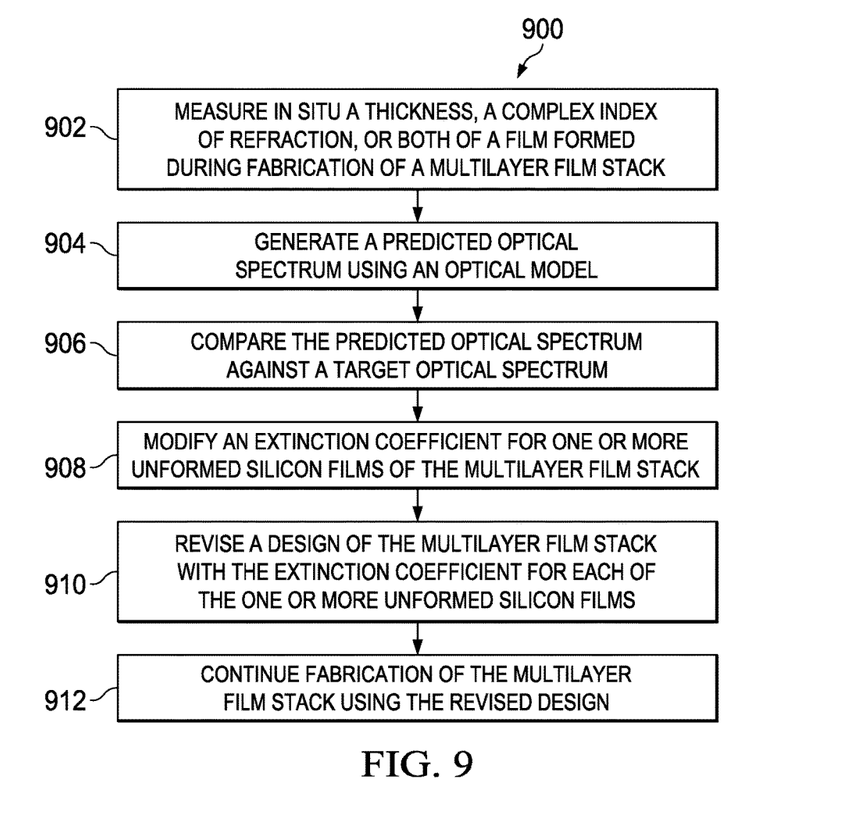
FIG. 9 is a schematic flowchart of an illustrative embodiment of a method for improving optical spectrum fidelity of an integrated computational element comprised of alternating films of silicon and an oxide of silicon.

Now referring primarily to FIG. 9, a schematic flowchart of an illustrative embodiment of a method 900 is presented for improving optical spectrum fidelity of an integrated computational element comprised of alternating films of silicon and an oxide of silicon. The integrated computational element is configured, upon completion, to process an optical spectrum of a sample to allow a prediction of a chemical constituent or property of a fluid, e.g., a production fluid from a wellbore. The method 900 includes a step 902 of measuring in situ a thickness, a complex index of refraction, or both of a film formed during fabrication of integrated computational element and a step 904 of generating a predicted optical spectrum using an optical model. The optical model considers the multilayer stack as-fabricated up to the formed film. The method 900 also includes a step 906 of comparing the predicted optical spectrum against a target optical spectrum. The method 900 involves a step 908 of selecting or modifying an extinction coefficient of one or more unformed silicon films of the integrated computational element. The method 900 also includes a step 910 of revising a design of the integrated computational element with the extinction coefficient selected for each of the one or more unformed silicon films. The method 900 involves a step 912 of continuing fabrication of the integrated computational element using the revised design.

In some embodiments, the method 900 further includes iteratively repeating, for each film formed during fabrication of the integrated computational element, the step 902 of measuring in situ, the step 904 of generating the predicted optical spectrum, the step 906 of comparing the predicted optical spectrum, the step 908 of selecting or modifying the extinction coefficient, the step 910 of revising the design, and the step 912 of continuing fabrication. In other embodiments, the step 904 of generating the predicted optical spectrum includes a step of storing the measured thickness, the measured complex index of refraction, or both and a step of interpolating data points to predict and optical spectrum for the integrated computational element if completed as originally specified in the design. The interpolation may occur based on empirical data from other integrated computational elements.

The step 912 of continuing fabrication of the integrated computational element, in some embodiments, includes modifying the power of an ion-beam generator to modify the extinction coefficient of a silicon film during formation. In other embodiments, the step 912 of continuing fabrication of the integrated computational element includes forming a film of hydrogenated amorphous silicon. In still other embodiments, the step 912 of continuing fabrication of the integrated computational element includes forming a film of silicon carbide alloy, $Si_{1-x-y-z}C_xH_yF_z$ where x+y+z<1 and x is non-zero.

Figure 10:
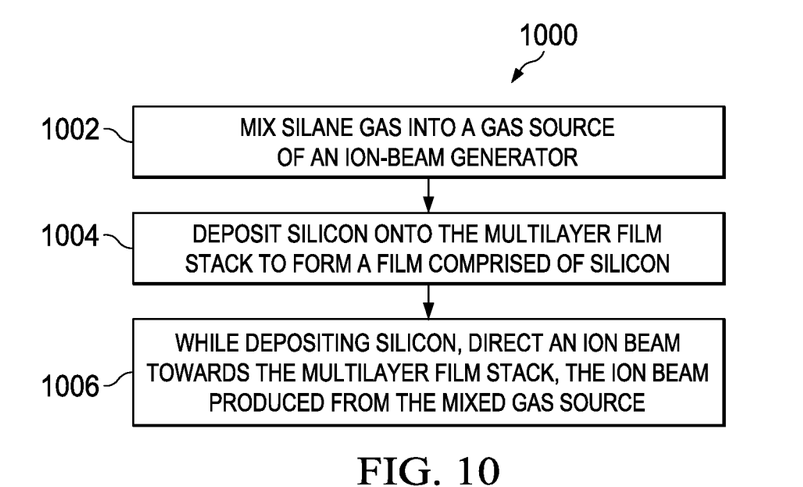
FIG. 10 is a schematic flowchart of an illustrative embodiment for continuing fabrication of an integrated computational element using a revised design.
Figure 11:
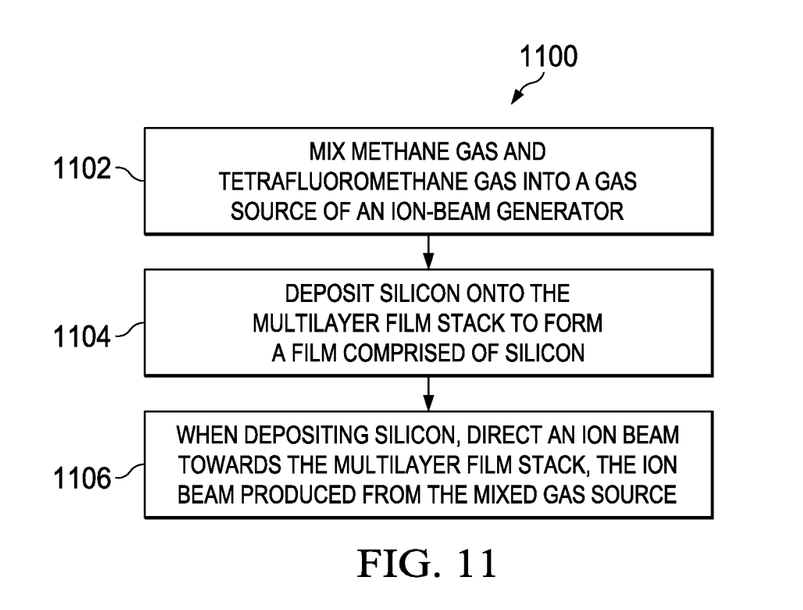
FIG. 11 is another schematic flowchart of an illustrative embodiment for continuing fabrication of an integrated computational element using a revised design.

Now referring primarily to FIG. 10, but also to FIG. 9, a schematic flowchart of an illustrative embodiment of a method 1000 is depicted for continuing fabrication of the integrated computational element using the revised design. The method 1000 includes a step 1002 of mixing silane gas into a gas source of an ion-beam generator and a step 1004 of depositing silicon onto the integrated computational element to form a film comprised of silicon. The method also involves a step 1006 of directing an ion-beam towards the integrated computational element while depositing silicon. The ion beam is produced from the mixed gas source by the ion-beam generator. FIG. 11 shows another embodiment of a method 1100 for continuing fabrication of the integrated computational element using the revised design. The method 1100 includes a step 1102 of mixing methane gas and tetrafluoromethane into a gas source of an ion-beam generator and step 1104 of depositing silicon onto the integrated computational element to form a film comprised of silicon. The method also involves a step 1106 of directing an ion-beam towards the integrated computational element while depositing silicon. The ion beam is produced from the mixed gas source by the ion-beam generator.

A performance metric for quantifying optical spectrum fidelity of an integrated computational element may be used. The performance metric may include, but is not limited to, minimum prediction error, standard error of calibration (SEC), standard error of performance (SEP), sensitivity, slope of the calibration curve, signal-to-noise ratio, and mean transmission value corresponding to the particular characteristic or analyte of interest. For example, the SEC for each integrated computational element design may be calculated by taking the square root of the sum of squares between the known value for the analyte of interest and the predicted value as derived from the optical spectrum of the integrated computational element design.

In addition to the embodiments described above, many examples of specific combinations are within the scope of the disclosure, some which are detailed below.

Example 1

A method for improving optical spectrum fidelity of a integrated computational element fabricated on a substrate, the method comprising:
  measuring in situ a thickness, a complex index of refraction, or both of a film formed during fabrication of the integrated computational element;
  generating a predicted optical spectrum using an optical model, the optical model to represent the integrated computational element as-fabricated;
  comparing the predicted optical spectrum against a target optical spectrum;
  revising a design of the integrated computational element with respect to a thickness, a complex index of refraction, or both for each of the one or more unformed films;
  continuing fabrication of the integrated computational element using the revised design; and
  wherein integrated computational element is configured, upon completion, to transmit an optical spectrum representing a chemical constituent of a fluid.

Example 2

The method of example 1, further comprising iteratively repeating, for each film formed during fabrication of the integrated computational element, the steps of measuring in situ, generating the predicted optical spectrum, comparing the predicted optical spectrum against a target optical spectrum, revising the design, and continuing fabrication.

Example 3

The method of example 1 or example 2, wherein generating the predicted optical spectrum using the optical model comprises:
  storing into a database the measured thickness, the measured complex index of refraction, or both for all formed films of the integrated computational element;
  storing into the database an expected thickness, an expected complex index of refraction, or both for all unformed films of the integrated computational element;

developing an optical model from the database, the database to represent an as-fabricated state of the integrated computational element;
calculating the predicted optical spectrum using the optical model; and
wherein the expected thickness and the expected complex index of refraction are specified by the design of the integrated computational element.

Example 4

The method of example 1 or any of examples 2-3, wherein selecting the steps of revising a design and continuing fabrication comprises determining a power of an ion-beam generator.

Example 5

The method of example 1 or any of examples 2-4, wherein revising the design comprises altering the number of unformed films of the integrated computational element.

Example 6

A system for improving optical spectrum fidelity of an integrated computational element fabricated on a substrate, the system comprising:
a chamber for isolating the substrate;
a mass-flux generator configured to direct a mass flux of elements, molecules, or combination thereof within the chamber towards the substrate, the mass-flux generator operable to form a film of the integrated computational element;
a precision measurement device configured to measure a thickness, a complex index of refraction, or both of the film formed by the mass-flux generator, the precision measurement device coupled to the chamber for in situ measurement of the thickness, the complex index of refraction, or both;
a computational unit coupled to the mass-flux generator to control film formation during fabrication of the integrated computational element and coupled to the precision measurement device to control measurement of the thickness, the complex index of refraction, or both;
wherein the computational unit comprises one or more processors and one or more memories;
and wherein the one or more processors and one or more memories are operational to generate a predicted optical spectrum of the as-fabricated integrated computational element and compare the predicted optical spectrum to a target optical spectrum.

Example 7

The system of example 6, the system further comprising:
an ion-beam generator configured to direct an ion beam of elements, molecules, or combination thereof within the chamber towards the substrate;
wherein ion-beam generator is operable to impinge the ion beam upon the film during formation; and
wherein the ion-beam generator is coupled to the computational unit, for controlling the ion-beam generator during fabrication of the integrated computational element.

Example 8

The system of example 6 or example 7, wherein the mass-flux generator comprises one or more mass sources of elemental silicon and one or more mass sources of silicon dioxide, the mass-flux generator operational to produce films of silicon and silicon dioxide.

Example 9

The system of example 7 or example 8, wherein the ion-beam generator comprises a silane gas source, the silane gas source operational to form films of hydrogenated amorphous silicon.

Example 10

The system of example 7 or example 8, wherein the ion-beam generator comprises a methane gas source and a tetrafluoromethane gas source, the methane gas source and the tetrafluoromethane gas source operational to form films of silicon carbide alloy, $Si1-x-y-zC_xH_yF_z$ where $x+y+z<1$ and x is non-zero.

Example 11

The system of example 6 or any of examples 7-10, wherein the precision measurement device comprises an ellipsometer.

Example 12

The system of example 6 or any of examples 7-10, wherein the precision measurement device comprises a spectrometer, the spectrometer configured to measure an optical spectrum of the as-fabricated integrated computational element.

Example 13

A method for improving optical-spectrum fidelity of an integrated computational element comprised of alternating films of silicon and an oxide of silicon, the method comprising:
measuring in situ a thickness, a complex index of refraction, or both of a film formed during fabrication of the integrated computational element;
generating a predicted optical spectrum using an optical model;
comparing the predicted optical spectrum against a target optical spectrum;
modifying an extinction coefficient of one or more unformed silicon films of the integrated computational element;
revising a design of the integrated computational element with the extinction coefficient selected for each of the one or more unformed silicon films;
continuing fabrication of the integrated computational element using the revised design; and
wherein the integrated computational element is configured, upon completion, to transmit an optical spectrum representing a chemical constituent of a fluid.

Example 14

The method of example 13, the method further comprising iteratively repeating, for each film formed during fabrication of the integrated computational element, the steps of measuring in situ, generating the predicted optical spectrum, comparing the predicted optical spectrum, modifying the extinction coefficient, revising the design, and continuing fabrication.

Example 15

The method of example 13 or example 14, wherein generating the predicted optical spectrum using the optical model comprises:
  storing the measured thickness, the measured complex index of refraction, or both; and
  based on empirical data from other integrated computational elements, interpolating data points to predict an optical spectrum for the integrated computational element if completed as an original design specified.

Example 16

The method of example 13 or any of examples 14-15, wherein continuing fabrication of the integrated computational element comprises modifying a power of an ion-beam generator to modify the extinction coefficient of a silicon film during formation.

Example 17

The method of example 13 or any of examples 14-15, wherein continuing fabrication of the integrated computational element comprises:
  mixing silane gas into a gas source of an ion-beam generator;
  depositing silicon onto the integrated computational element to form a film comprised of silicon; and
  while depositing silicon, directing an ion beam towards the integrated computational element, the ion beam produced from the mixed gas source by the ion-beam generator.

Example 18

The method of example 13 or any of examples 14-15, wherein continuing fabrication of the integrated computational element comprises forming a film of hydrogenated amorphous silicon.

Example 19

The method of example 13 or any of examples 14-15, wherein continuing fabrication of the integrated computational element comprises:
  mixing methane gas and tetrafluoromethane gas into a gas source of an ion-beam generator;
  depositing silicon onto the integrated computational element to form a film comprised of silicon; and
  while depositing silicon, directing an ion beam towards the integrated computational element, the ion beam produced from the mixed gas source by the ion-beam generator.

Example 20

The method of example 13 or any of examples 14-15, wherein continuing fabrication of the integrated computational element comprises forming a film of silicon carbide alloy, $Si_{1-x-y-z}C_xH_yF_z$ where $x+y+z<1$ and x is non-zero.

Example 21

A method for improving optical spectrum fidelity of a integrated computational element fabricated on a substrate, the method comprising:
  measuring in situ a thickness, a complex index of refraction, or both of a film formed during fabrication of the integrated computational element;
  generating a predicted optical spectrum using an optical model, the optical model to represent the integrated computational element as-fabricated;
  comparing the predicted optical spectrum against a target optical spectrum;
  revising a design of the integrated computational element with respect to a thickness, a complex index of refraction, or both for each of the one or more unformed films;
  continuing fabrication of the integrated computational element using the revised design; and
  wherein integrated computational element is configured, upon completion, to transmit an optical spectrum representing a chemical constituent of a production fluid from a wellbore.

Example 22

The system of example 6 or any of examples 7-12, wherein the precision measurement device is configured to measure a thickness and comprises a quartz crystal monitoring device.

Example 23

The system of example 6 or any of examples 7-12, wherein the precision measurement device is configured to measure a thickness and comprises an optical monitoring device.

Example 24

The system of example 6 or any of examples 7-12, wherein the precision measurement device comprises a plurality of precision measure devices.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order or simultaneous where appropriate. Where appropriate, aspects of any of the examples described above may be combined with aspects of any of the other examples described to form further examples having comparable or different properties and addressing the same or different problems.

It will be understood that the above description of the embodiments is given by way of example only and that various modifications may be made by those skilled in the art. The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method for adjusting optical spectrum fidelity of an integrated computational element fabricated on a substrate, the method comprising:
    measuring in situ a thickness and a complex index of refraction of a film formed during fabrication of the integrated computational element;
    generating a predicted optical spectrum using an optical model, the optical model comprising the measured thickness and complex index of refraction for the film, and an expected thickness and complex index of refraction for each of one or more unformed films of the integrated computational element as-fabricated;
    comparing the predicted optical spectrum against a target optical spectrum;
    revising the optical model with respect to the extinction coefficient for each of the one or more unformed films;
    continuing fabrication of the integrated computational element via modifying a power of an ion-beam generator during formation to alter an extinction coefficient based on the revised optical model without changing a thickness of a film; and
    wherein the integrated computational element is configured, upon completion, to transmit an optical spectrum representing a chemical constituent of a fluid.

2. The method of claim 1, further comprising: iteratively repeating, for each film formed during fabrication of the integrated computational element, the steps of measuring in situ, generating the predicted optical spectrum, comparing the predicted optical spectrum against a target optical spectrum, revising the design, and continuing fabrication.

3. The method of claim 1, wherein generating the predicted optical spectrum using the optical model comprises:
    storing into a database the measured thickness, the measured complex index of refraction, or both for all formed films of the integrated computational element;
    storing into the database an expected thickness, an expected complex index of refraction, or both for all unformed films of the integrated computational element;
    developing an optical model from the database, the database to represent an as-fabricated state of the integrated computational element;
    calculating the predicted optical spectrum using the optical model; and
    wherein the expected thickness and the expected complex index of refraction are specified by the design of the integrated computational element.

4. The method of claim 1, wherein revising the design comprises altering the number of unformed films of the integrated computational element.

5. A method for adjusting optical-spectrum fidelity of an integrated computational element comprised of alternating films of silicon and an oxide of silicon, the method comprising:
    measuring in situ a thickness and complex index of refraction of one of the alternating films formed during fabrication of the integrated computational element;
    generating a predicted optical spectrum using an optical model comprising the measured thickness and complex index of refraction, and an expected thickness and complex index of refraction for each of one or more unformed films of the integrated computational element as-fabricated;
    comparing the predicted optical spectrum against a target optical spectrum;
    modifying an extinction coefficient of the one or more unformed silicon films of the integrated computational element and re-comparing the predicted optical spectrum to the target optical spectrum until the extinction;
    revising a design of the integrated computational element with the modified extinction coefficient for each of the one or more unformed silicon films;
    continuing fabrication of the integrated computational element via modifying a power of an ion-beam generator during formation to alter an extinction coefficient based on the revised design of the integrated computational element without changing a thickness of one of the films of silicon or oxide of silicon; and
    wherein the integrated computational element is configured, upon completion, to transmit an optical spectrum representing a chemical constituent of a fluid.

6. The method of claim 5, the method further comprising: iteratively repeating, for each film formed during fabrication of the integrated computational element, the steps of measuring in situ, generating the predicted optical spectrum, comparing the predicted optical spectrum, modifying the extinction coefficient, revising the design, and continuing fabrication.

7. The method of claim 5, wherein generating the predicted optical spectrum using the optical model comprises:
    storing the measured thickness, the measured complex index of refraction, or both; and
    based on empirical data from other integrated computational elements, interpolating data points to predict an optical spectrum for the integrated computational element if completed as an original design specified.

8. The method of claim 5, wherein continuing fabrication of the integrated computational element comprises:
    mixing silane gas into a gas source of the ion-beam generator;
    depositing silicon onto the integrated computational element to form at least one of the films of silicon; and
    while depositing silicon, directing an ion beam towards the integrated computational element, wherein the ion beam is produced from the gas source by the ion-beam generator.

9. The method of claim 5, wherein continuing fabrication of the integrated computational element comprises forming a film of hydrogenated amorphous silicon.

10. The method of claim 5, wherein continuing fabrication of the integrated computational element comprises:
    mixing methane gas and tetrafluoromethane gas into a gas source of an ion-beam generator;
    depositing silicon onto the integrated computational element to form at least one of the films of silicon; and
    while depositing silicon, directing an ion beam towards the integrated computational element, wherein the ion beam is produced from the gas source by the ion-beam generator.

11. The method of claim 5, wherein continuing fabrication of the integrated computational element comprises forming a film of silicon carbide alloy, $Si_{1-x-y-z}C_xH_yF_z$, where $x+y+z<1$ and x is non-zero.

* * * * *